United States Patent [19]

Crotzer et al.

[11] Patent Number: 5,273,777
[45] Date of Patent: Dec. 28, 1993

[54] METHOD FOR MANUFACTURING HYGRISTORS

[75] Inventors: David R. Crotzer, Glen Gard; Roberto Falcone, Little Falls, both of N.J.

[73] Assignee: Victory Engineering Corp, Springfield, N.J.

[21] Appl. No.: 681,987

[22] Filed: Apr. 8, 1991

[51] Int. Cl.⁵ .............................................. B05D 5/12
[52] U.S. Cl. ...................................... 427/101; 29/620; 427/125; 427/430.1
[58] Field of Search .................. 29/620; 427/101, 122, 427/125, 384, 430.1

[56] References Cited

U.S. PATENT DOCUMENTS 3,930,896  1/1976  Takahama et al. ............. 427/101 X
4,352,359  10/1982  Larimore et al. ................... 128/640
4,849,251  7/1989  Tanaka ................................. 427/101

Primary Examiner—Michael Lusignan
Attorney, Agent, or Firm—Thomas R. Morrison

[57] ABSTRACT

A method for manufacturing hygristors includes preparing a hygroscopic gel containing a substantially greater proportion of carbon than the prior art, and milling the gel for a period of at least 24 hours to produce a smooth mixture. Substrates are dipped into the milled gel at controlled rates to coat the substrates. The coated substrates are cured under controlled temperature and humidity. Adhesion of the coating is improved by the smoother mixture resulting from the longer milling time, and by the differences in components of the mixture compared to the prior art. Long term stability and dynamic range are both increased.

17 Claims, 4 Drawing Sheets

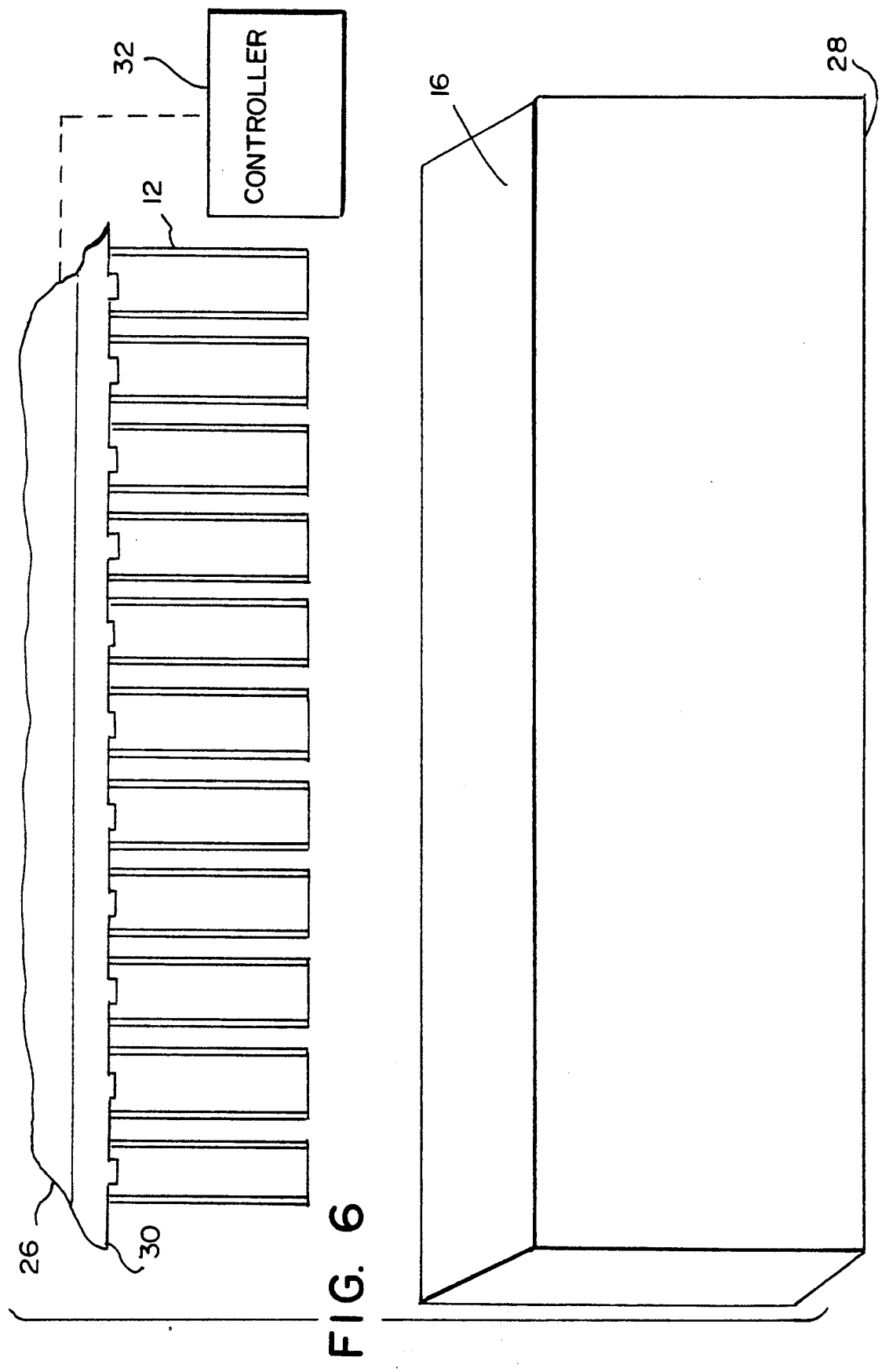

RH SENSORS
02/14/90 1838-41 UT

METHOD FOR MANUFACTURING HYGRISTORS

BACKGROUND OF THE INVENTION

The present invention relates to the manufacture of carbon resistors, and more particularly to the manufacture of carbon resistors whose conductivity varies with ambient conditions such as humidity, and still more particularly with the manufacture of hygristors.

The manufacture and use of such resistors are well established and are described fully by S. L. Stine (U.S. Army Material Support Agency, Electronic Command, Fort Monmouth, N.J.): "Principles and Methods of Measuring Humidity in Gasses;" Volume 1—"Humidity and Moisture Control in Science and Industry"—'International Symposium on Humidity, 1963"—Reinhold; Library of Congress Catalog No. 65-13613. Such atmospherically controlled variable resistors are, for example, frequently used as hygristors in meteorological radiosondes, to measure atmospheric humidity for weather analysis.

Major problems associated with hygristors manufactured by conventional means are that they are usable over a limited range of ambient conditions and have broad operating tolerances and therefore do not permit accurate measurement in either the high or low ends of the scale in which they are operable.

OBJECTS AND SUMMARY OF THE INVENTION

Accordingly, it is an object of the invention to provide a method for manufacturing hygristors which overcomes the drawbacks of the prior art.

It is a further object of the invention to provide a method for manufacturing hygristors that are usable over a broader operating range and display smoother response curves relative to conventionally manufactured hygristors.

It is a further object to provide a method of manufacture that consistently yields a higher percentage of quality hygristors having uniform operating characteristics.

It is a still further object of the invention to provide a method for manufacturing hygristors which reduces the processing time and reduces the processing steps.

It is a still further object of the invention to provide a method for manufacturing hygristors which reduces the labor required to perform the process.

Briefly stated, the present invention provides a method for manufacturing hygristors which includes preparing a hygroscopic gel containing a substantially greater proportion of carbon than the prior art, and milling the gel for a period of at least 24 hours to produce a smooth mixture. Substrates are dipped into the milled gel at controlled rates to coat the substrates. The coated substrates are cured under controlled temperature and humidity. Adhesion of the coating is improved by the smoother mixture resulting from the longer milling time, and by the differences in components of the mixture compared to the prior art. Long term stability and dynamic range are both increased.

According to an embodiment of the invention, there is provided a method for manufacturing a hygristor comprising: preparing a substrate, mixing a hygroscopic conductive gel, blending the hygroscopic conductive gel for a minimum of 24 hours, coating the substrate with the hygroscopic conductive gel, and curing the coating.

According to a feature of the invention, there is provided a method of manufacturing hygristors comprising: mixing a hygroscopic conductive gel, the mixing the hygroscopic conductive gel includes mixing together, exclusive of water, the following by percentage of weight: hydroxyethylcellulose—from about 19.75 percent to about 25.77 percent, nonyl phenyl polyethylene glycol ether, nonionic (NPX) nonyl phenol oxylate anhydrous—from about 2.23 percent to about 3.03 percent, (TYLOXANOL) USP) (oxyethylated teriary octylphenol formaldehyde polymer)—from about 26.94 percent to about 49.92 percent, carbon—from about 32.99 percent to about 41.04 percent, and Polyethylene Sorbitol—from about 4.45 percent to about 6.64 percent.

According to a further feature of the invention, there is provided a method for manufacturing hygristors comprising: molding a substrate of a dielectric material, and metallizing, with silver, opposing edges along a longitudinal axis of the substrate.

According to a further feature of the invention, there is provided a method for manufacturing hygristors comprising, dipping a substrate into a hygroscopic conductive gel at a controlled rate, holding the substrate in the hygroscopic conductive gel for a period, raising the substrate from the hygroscopic conductive gel at a controlled rate, the dipping rate being from about 7 seconds to about 8 seconds per inch, the holding period being from about 30 seconds to about 120 seconds, and the raising rate being from about 8 seconds to about 9 seconds per inch.

According to a still further feature of the invention, there is provided a method of manufacturing hygristors, comprising: mixing a hygroscopic gel, the hygroscopic gel including from about 32.99 percent to about 41.04 percent carbon, exclusive of a water content of the hygroscopic gel, milling the hygroscopic gel for a predetermined time, coating a substrate with the hygroscopic gel, and curing the hygroscopic gel.

According to a still further feature of the invention, there is provided a hygristor, comprising: a substrate, metallized contacts along at least two edges of the substrate, a cured hygroscopic gel on the substrate between the metallized contacts, and the substrate being one of cast and molded.

The above and other objects features and advantages of the invention will become apparent from the following description of the preferred embodiment read in conjunction with the accompanying drawings, in which like reference numerals designate the same elements.

BRIEF DESCRIPTION OF THE DRAWINGS

FIG. 6 shows a rack of prepared hygristor substrates suspended above a dipping reservoir.

DETAILED DESCRIPTION OF THE PREFERRED EMBODIMENT

The present invention and the prior art have certain elements in common. The following general description provides a basis for understanding the differences.

Figure 1:
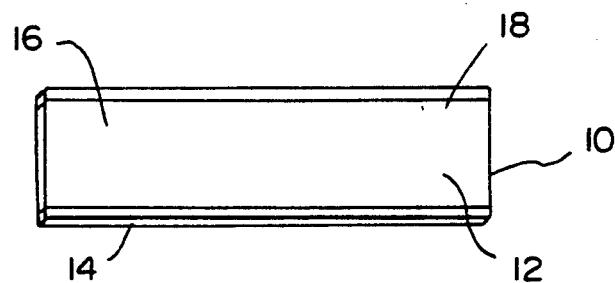
FIG. 1 is a top view of a typical hygristor.

Referring to FIG. 1, a hygristor 10 of the present invention, or the prior art, is a device whose electrical resistance varies with atmospheric humidity and temperature, so that if the temperature of the hygristor is kept constant, atmospheric humidity can be determined from the instantaneous resistance of hygristor 10.

Hygristor 10 is made up of a substrate 12 that may be of acrylic or other suitable material, whose opposing longitudinal conductive edges 14 are coated with a conductive material such as silver paint. A coating of hygroscopic gel 16 covers a substantial portion of substrate 12 between conductive edges 14. Hygroscopic gel 16 contains conductive carbon particles 18 that form an electrical path between conductive edges 14.

As ambient humidity increases, hygroscopic gel 16 swells, decreasing the relative density of carbon particles 18 and, as a result, increasing the electrical resistance between conductive edges 14. Decreased humidity causes a shrinkage of the hygroscopic gel 16, increasing the relative density of carbon particles 18 and, as a result, decreasing the resistance between conductive edges 14.

Briefly, hygristor 10 is produced by the following steps:
preparation of substrate 12,
mixing of hygroscopic gel 16,
coating substrate 12 with hygroscopic gel,
curing resultant hygristor 10, and
adjusting the resistance of hygristor 10.

Figure 2:
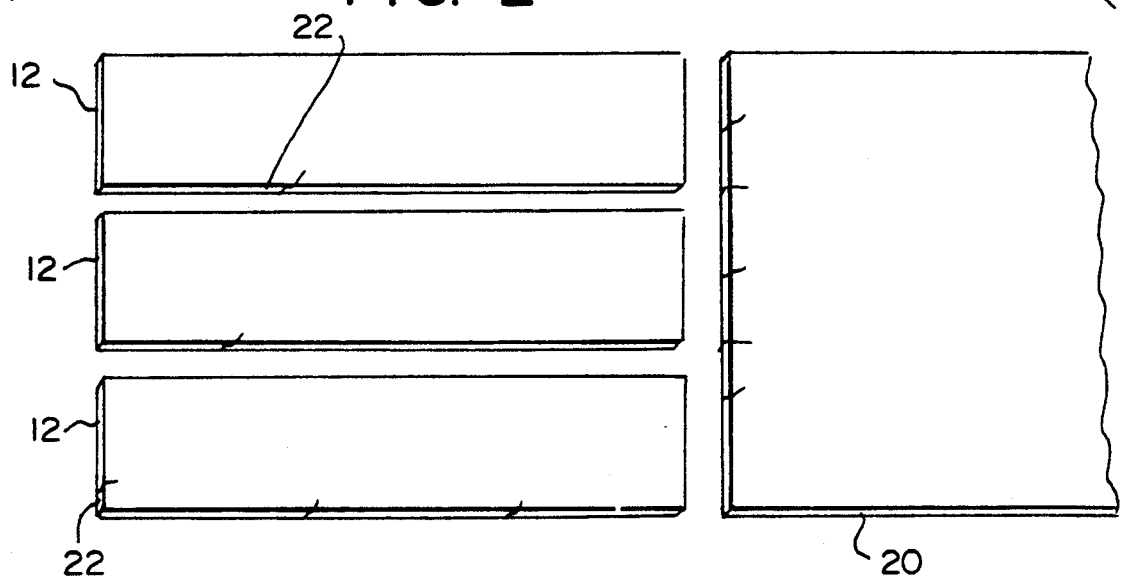
FIG. 2 shows hygristor substrates cut from large acrylic plastic sheets.

Referring to FIG. 2, substrate 12 of a conventional hygristor is cut from a large acrylic sheet 20, and is therefore subject to microscopic fractures 22 along the cut edges. These fractures can trap moisture, which can effect the operation of the completed hygristor.

Figure 3:
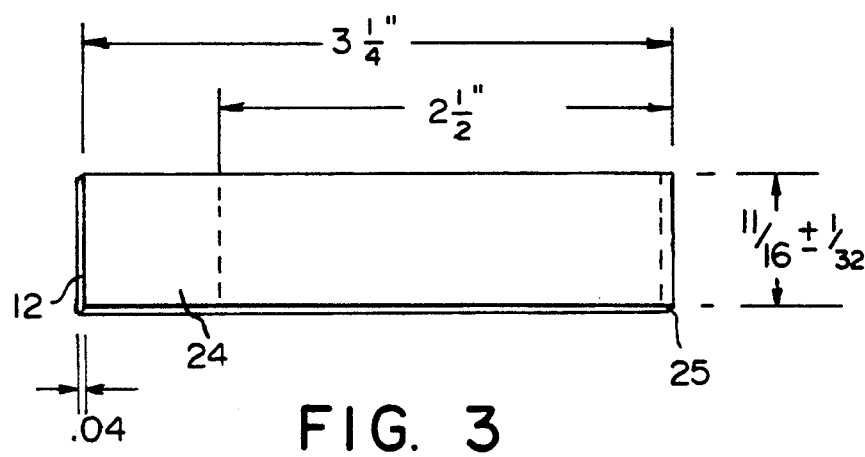
FIG. 3 shows a molded acrylic substrate of the present invention.

In FIG. 3 there is shown a substrate 12 that is molded individually of acrylic. A molded substrate, which is used in the preferred embodiment of the present invention, is not subject to the cut fractures 22 of FIG. 2. As shown in FIG. 3, substrate 12 is 3¾ inch long. This length includes a ½-inch handling portion 24 and a last ¼-inch portion 25 that are to be trimmed away afterward, thereby leaving a hygristor 10 with a standard size of 2½ inches long by 11/16±1/32 inch wide by 0.04 inch thick.

Figure 4:
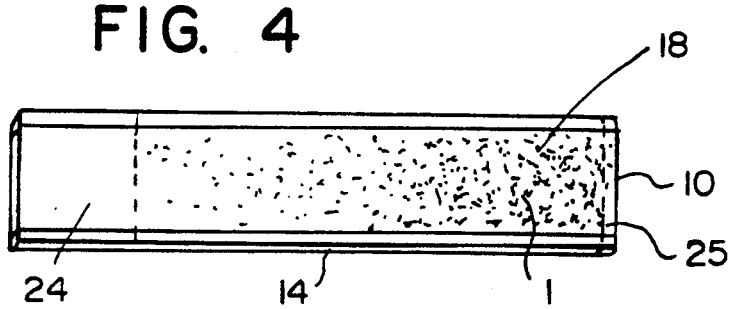
FIG. 4 shows the irregular pattern of relatively large carbon particles deposited on the substrate of a hygristor using conventional manufacturing methods.

Referring to FIG. 4, there is shown a hygristor 10 manufactured using conventional means as follows:

A. Substrate 12 preparation;

1. Substrate 12 is cut from a large acrylic sheet and cleaned of all traces of grease oil and dirt using conventional means 2. Conductive edges 14 3/32±1/64 inch wide are painted on substrate 12 with a 0.0003 to 0.0005 inch thickness of conductive silver paint, using care not to paint between the borders of conductive edges 14.

3. The painted conductive edges 14 are thoroughly dried under infra-red radiation.

4. Substrate 12 and conductive edges 14 are inspected for quality and accuracy.

5. Substrate 12 is washed in hot water and a mild detergent with a wetting agent, using vigorous agitation, and then rinsed in hot running water until no detergent bubbles appear for 5 minutes with agitation.

6. Prepared substrates 12 are rinsed carefully in and stored in running de-ionized water, arranged so that they do not touch each other and a free flow of de-ionized water is assured.

B. Hygroscopic gel 16 preparation

NOTES: The following procedure is performed in a dust free clean room that is temperature and humidity controlled and under a controlled ambient hood to maintain a ventilated dust, vapor and carbon dioxide free environment that is temperature controlled at 25±1 degrees C. and humidity controlled to 33±2 NIST trackable percent RH.

This procedure requires 10 days for completion and requires four mixing steps.

1. Prepare mixture 1:
Ingredients—HEC (hydroxyethylcellulose), Union Carbide—25 grams (stored under desiccants for at least 1 month before use)
De-ionized water—470 grams (de-ionized in Amberlite to a conductivity of 0.00000015 mhos or less)
(TERGITOL) nonyl phenyl polyethylene glycol ether, nonionic (NPX) (nonyl phenyl ethoxylate), anhydrous, Union Carbide and Carbon Corp.—4.12 grams a. While de-ionized water is hand stirred, (TERGITOL) nonyl phenyl polyethylene glycol ether is added drop by drop, stirring is continued for 15 minutes after all of the (TERGITOL) nonyl phenyl polyethylene glycol ether is added or until all of the (TERGITOL) nonyl phenyl polyethylene glycol ether appears to be in solution.

b. "Tergitol" solution is motor power stirred for 30 minutes at low speed so that no bubbles are formed.

c. Stirring rate is increased to high and HEC is sifted into the solution preventing clumps larger than 1/16 inch from entering (the rejected HEC clumps must be replaced by equal weight of usable HEC)

d. stirring is continued for 2 hours or until all of the HEC is in solution e. a jet of filtered air is used to break up surface foam and the resultant mixture 1 is covered and stored for 2 days to permit bubbles to disperse f. mixture 1 is examined, if a brown liquid separates from the solution, mixture 1 is discarded and a new mix is made using fresh materials. If the mix is clear, the gelled mixture is broken up by hand stirring and passed through a ¼ inch layer of Amberlite supported by a 200 mesh stainless steel screen in a 4 inch Buchner filter with a slight vacuum applied. This procedure is continued until the conductivity of mixture 1 is 0.0000002 mhos or less.

2. Prepare mixture 2;
Ingredients—(TRITON) (TYLOXAPOL) WR 1339 oxyethylated tertiary octylphenol formaldehyde polymer), Rohm and Hass Company—10:14 grams
carbon (70 percent "Elf 1, #0 percent "Elf 2") Godfrey L. Cabot, Inc.—5.75 grams
de-ionized water—120 grams a. 10.14 grams of (TRITON) oxyethylated tertiary octylphenol formaldehyde polymer is dissolved in 100 grams of hot de-ionized water.

b. (TRITON) oxyethylated tertiary octylphenol formaldehyde polymer solution is cooled, shaken with 50 grams of Amberlite, decanted and covered.
c. The (TRITON) oxyethylated tertiary octylphenol formaldehyde polymer mix is added to 20 grams of de-ionized water and hand stirred until thoroughly mixed.
d. Carbon is sifted into the (TRITON) oxyethylated tertiary octylphenol formaldehyde polymer solution, with larger carbon clumps discarded and replaced with equal weight of usable carbon, and hand stirred.

3. Prepare mixture 3;
Ingredients—mixture 1—80 grams
de-ionized water—210 grams
"Sorbitol" (Polyethylene, Polyethylene Sorbitol and related polyols) G2240, Atlas Powder Co.—2.7 grams
   a. 80 grams of mixture 1 is hand stirred while the de-ionized water is added.
   b. Hand stirring is continued while "Sorbitol" is added to the mixture.

4. Prepare mixture 4;
Ingredients—mixture 2 and mixture 3
   a. Mixture 2 is hand stirred while mixture 3 is added.
   b. The resultant mix is blended at moderate speed in a blender.
   c. A jet of filtered air is used to break up surface bubbles, and the resultant hygroscopic gel 16 is ball milled using stone balls of between ½ to ¾ inch for 2 hours.

C. Substrate 12 dipping;
1. Remove substrates 12 previously prepared from storage in running de-ionized water and dry them thoroughly under infra red radiation.
2. Install dried substrates 12 in a dipping rack 26, as shown in FIG. 6. The contact points 30 of dipping rack 26 with substrates 12 should be made of metal such as gold plated phosphor bronze and support substrates 12 by ¼ inch handling portion 24 with a minimum of contact.
3. Lower substrates 12 into dipping reservoir 28 that is filled with hygroscopic gel 16 and hold submerged for 10 seconds. Lift dipping rack 26 with substrates 12 out of dipping reservoir 28 at a precisely controlled constant rate of 2⅛ inches per 25 seconds.
4. Immediately on removal, expose dipping rack 26, and wet hygristors 10 to a brisk stream of moving air having a temperature of $23 \pm 3$ degrees C. and a relative humidity of $33 \pm 3$ percent. Hygristors 10 appear dry after 5 minutes, but must be maintained in this atmosphere of moving air for at least 24 hours prior to final adjustment.

Connecting a Wheatstone bridge across conducting edges 14 of a centrally located hygristor 10 on dipping rack 26 to determine when hygristors 10 are fully dried. If, under frequent observation, the measured resistance remains within 100 ohms for a period of 4 hours, hygristors 10 are considered to be fully dried and are ready to be cut and adjusted.

Figure 7:
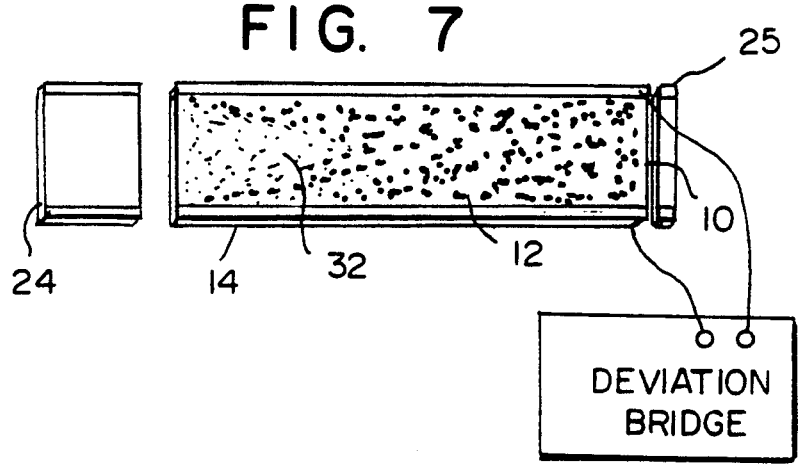
FIG. 7 shows the final calibration of a completed hygristor using conventional manufacturing methods.

D. Hygristor 10 adjustment, refer to FIG. 7;
1. The last ¼-inch portion 25 of hygristor 10 to leave dipping reservoir 28 and the ¼-inch handling portion 24 are trimmed from hygristor 10.
2. A deviation bridge using 60 cycle AC current is connected across conductive edges 14 to measure the resistance of each hygristor with ambient conditions of $23 \pm 3$ degrees C. and $33 \pm 3$ percent RH. Calibration adjusts the resistance of each hygristor upward. The initial resistance of each hygristor must be below the required operating resistance of a calibrated hygristor 10 for this ambient condition. If the initial resistance of any hygristor 10 is higher than the required operating resistance, it is discarded.
3. Hygristor 10 is adjusted to the required resistance 2 by forming an abrasion or scrape 32 in hygroscopic gel 16 as shown in FIG. 7 until the deviation bridge indicates 10,000 to 10,400 ohms.
4. Adjusted hygristor 10 is stored under the same ambient conditions for 8 to 10 days, during which frequent checks of its resistance are made. The resistance of the hygristor can be expected to decrease from 3 to 4 percent during this time.

Figure 5:
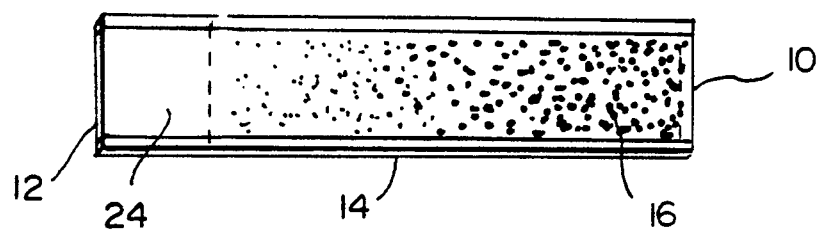
FIG. 5 shows the dense smoothly graded fine carbon particles deposited on the substrate of a hygristor using the manufacturing method of the present invention.

Referring to FIG. 5, there is shown a hygristor 10 manufactured in accordance with the present invention.
A. Substrate 12 preparation;
1. A molded or cast substrate 12 is selected and cleaned of all traces of grease oil and dirt using an enzyme detergent such as Turgizyme.
2. The substrate is masked on both sides, leaving conductive edges 14 bare for spraying.
3. Conductive edges 14 $3/32 \pm 1/64$ inch wide on both sides are sprayed on substrate 12 with a 0.005 to 0.007 inch thickness of conductive silver paint, including the edges.
4. The painted conductive edges 14 are thoroughly dried under infra-red radiation for $60 \pm 5$ minutes.
5. Substrate 12 and conductive edges 14 are inspected for quality and accuracy.
6. Substrate 12 is washed in hot water and a mild detergent with a wetting agent using vigorous agitation and then rinsed in hot running water until no detergent bubbles appear for 5 minutes with agitation.
7. Prepared substrates 12 are rinsed carefully in and stored in running de-ionized water, arranged so that they do not touch each other and a free flow of de-ionized water is assured.

B. Hygroscopic gel 16 preparation
NOTES: The following procedure is performed in a dust free clean room under a controlled ambient hood to maintain a ventilated dust, vapor and carbon dioxide free environment that is temperature controlled at $25 \pm 1$ degrees C. and humidity controlled to $33 \pm 2$ percent RH.

This procedure requires 5 days for completion and requires three mixing steps. The prior-art procedure requires 10 days. The reduced time of 5 days required for the completion of the current procedure results from the reduced preparation time for the final ingredients, 4 days, plus one day for final mixing. The present procedure provides a smoother, more homogeneous product.

1. Prepare mixture 1;
Ingredients—HEC (hydroxyethylcellulose), Union Carbide—25 gms (stored under desiccants for at least 1 month before use)
de-ionized water—470 gms (de-ionized to a conductivity of 0.00000015 mhos or less)
(TERGITOL) (Nonyl phenolpolyethylene glycol ether), nonionic NPX, anhydrous, Union Carbide and Carbon Corp.—2.9 gms
   a. While a room temperature of between 20 to 25 degrees C. is maintained de-ionized water is hand stirred, (TERGITOL) nonyl phenyl polyethylene glycol ether added drop by drop, stirring is continued for $15 \pm 5$ minutes after all of the (TER- GITOL) nonyl phenyl polyethylene glycol ether is added or until all of the (TERGITOL) nonyl phenyl polyethylene glycol ether appears to be in solution.
  b. (TERGITOL) nonyl phenyl polyethylene glycol ether solution is motor power stirred at low speed (500±100 rpm) so that no bubbles are formed for 30±5 minutes.
  c. Stirring rate is increased to high (2,000±200 rpm) and HEC is sifted into the solution preventing clumps larger than 1/16 inch from entering. (The rejected HEC clumps must be replaced by equal weight of usable HEC.)
  d. Stirring is continued for 2 hours or until all of the HEC is in solution.
  e. A jet of filtered air is used to break up surface foam and the resultant mixture 1 is covered and stored for 2 days±5 hrs to permit bubbles to disperse.
  f. Mixture 1 is examined, if a brown liquid separates from the solution, mixture 1 is discarded and a new mix is made using fresh materials. If the mix is clear, the gelled mixture is storable in a pyrex beaker up to one month or until algae appears.
2. Prepare mixture 2:
Ingredients—(TRITON) (TYLOXAPOL) WR—1339 oxyethylated tertiary octylphenol formaldehyde polymer Rohm and Hass Company—10 gms carbon (Furnace black), Cabot—660R Regal—11.4 gms
de-ionized water—479 gms
"Sorbitol" (Polyoxyethylene, Polyoxyethylene Sorbitol and related polyols)—Atlas Powder Co.—1.70 gms—liquid
mixture 1—140 gms—liquid
Amberlite—50 gms
  a. 10 gms of (TRITON) oxyethylated tertiary octylphenol formaldehyde polymer polyethylene glycol ether is dissolved in 100 gms of heated de-ionized water (30±2 degrees C.).
  b. (TRITON) oxyethylated tertiary octylphenol formaldehyde polymer solution is cooled, shaken with 50 grams of Amberlite, decanted and covered. The Amberlite is discarded.
  c. Carbon is sifted into the (TRITON) oxyethylated tertiary octylphenol formaldehyde polymer solution, with larger carbon clumps discarded and replaced with equal weight of usable carbon, and hand stirred.
  d. Mixture 1 is hand stirred in a ball milling crock while the (TRITON) oxyethylated tertiary octylphenol formaldehyde polymer/carbon mix is added.
  e. Hand stirring is continued while de-ionized water and "Sorbitol" are added.
  f. The resultant hygroscopic gel 16 is ball milled under power using ceramic balls of ½ to ¼ inch in diameter for at least 24 hours, or until homogeneity of the mix is observed. Longer periods of milling are beneficial.
  g. Five test substrates are coated using the following procedure and the coating inspected for correct dispersion and density.
C. Substrate 12 dipping;
  1. Substrates 12 previously prepared are removed from storage in running de-ionized water and dried thoroughly under infrared radiation.
  2. Dried substrates 12 are then installed in a dipping rack 26, as shown in FIG. 6. Contact points 30 of the dipping rack 26 with substrates 12 should be made of metal such as gold plated phosphor bronze and support substrates 12 by ⅛ inch handling portion 25 with a minimum of contact.
  3. Substrates 12 are lowered into dipping reservoir 28, filled with hygroscopic gel 16, under the control of controller 32 at a rate of about 1 inch per 7 seconds and is held submerged for 30 seconds. Controlled by controller 32, dipping rack 26 lifts substrates 12 out of dipping reservoir 28 at a rate of about 1 inch per 7 seconds.

Figure 8:
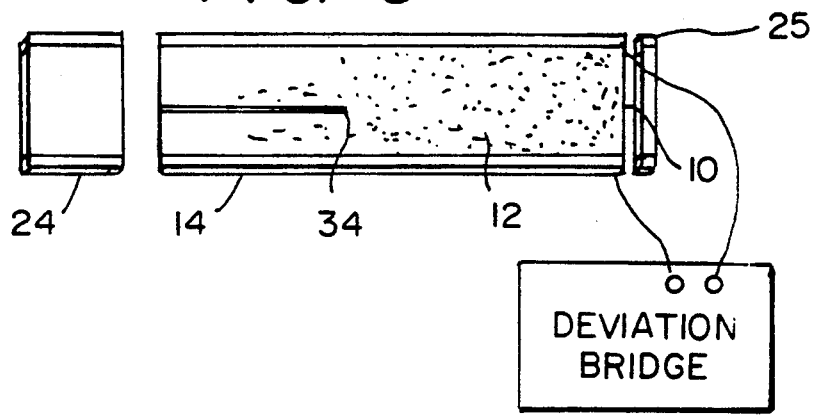
FIG. 8 shows the final calibration of a completed hygristor using the manufacturing method of the present invention.

In another embodiment of the invention, hygristors may be lowered into hygroscopic gel 16 individually by hand. However, the rates mentioned earlier are the same.
  4. Immediately on removal, dipping rack 26, and wet hygristors 10 are exposed to a brisk stream of moving air having a temperature of 25±2 degrees C. and a relative humidity of 33±2 percent. When hygristors 10 are dry enough to handle, they are removed from dipping rack 26 and laid out to dry. To determine when hygristors 10 are fully dried, the resistance of a representative sampling of drying hygristors 10 is measured across conductive edges 14 using a Wheatstone bridge. The resistance of adequately dried hygristors 10 is between 1,800 and 2,200 ohms. When dry, hygristors 10 are ready to be cut and adjusted.
D. Hygristor 10 adjustment, refer to FIG. 8:
  1. The last ⅛-inch portion 25 of hygristor 10 to leave dipping reservoir 28 and the ⅛-inch handling portion 24 are cut from hygristor 10. Resistance of hygristor 10 increases to between 4,000 to 6,000 ohms.
  2. A deviation bridge using 60 cycle AC current is connected across conductive edges 14 to measure the resistance of each hygristor 10 with ambient conditions of 25±2 degrees C. and 33±2 percent RH. The resistance must be below the required operating resistance of a calibrated hygristor 10 for this ambient condition. If the resistance of any hygristor 10 is high, it is discarded.
  3. Hygristor 10 is adjusted to the required resistance by forming a scratch 34 in hygroscopic gel 16, as shown in FIG. 8, until the deviation bridge indicates 9,600 ohms maximum.
  4. Adjusted hygristors 10 are stored under the same ambient conditions for 8 to 10 days during which frequent checks of its resistance are made. The resistance of the hygristor can be expected to increase from 3 to 4 percent during this time.

The major improvements by the present invention over the prior art are as follows:
  1. Cast or molded substrate 12—a molded or cast acrylic substrate 12 is not subject to the cut fractures 22 at cut edges such as found in prior art substrates 12 cut from sheet acrylic. The absence of such cut fractures may account for an improvement in dynamic range of the present invention.
  2. Conductive edges 14—a greater thickness of silver on the conductive edges, at least twice as thick as in the prior art, assures better electrical contact between conductive edges 14 and hygroscopic gel 16.
  3. Hygroscopic gel 16, is made by a different procedure and with different proportions of materials. In the prior-art, four mixing steps are required in the preparation of the hygroscopic gel, while the present invention simplifies the procedure to two steps. The improved formulation used in the present invention contains a higher proportion of carbon to the other ingredients as compared to the formulation of the prior art. This, as well as extended ball milling of the formulation following mixing, at least 24 hours, compared to the 2.5 hours of the conventional method, yields a wetter, denser, more conductive suspension of finer carbon particles 18, allowing the application of a thinner hygroscopic gel. This results in shorter response times to changes in relative humidity and less hysteresis error. A more even distribution of suspended carbon particles 18 in hygroscopic gel 16 assures improved consistency between manufactured hygristors, with fewer discards, which increases the adhesion/reducing resistance spreads in manufacturing.

A comparison of the proportions by percent of the dry components of the hygroscopic gel coating of the conventional hygristor with those of the present invention is presented in the following table:

| | Hygristor Components by Percent | | |
|---|---|---|---|
| | CONVENTIONAL | PRESENT INVENTION | |
| COMPONENT | HYGRISTOR | MIN | MAX |
| HEC | 17.20 | 19.75 | 25.77 |
| TERGITOL | 2.83 | 2.23 | 3.03 |
| TRITON | 43.61 | 26.94 | 49.92 |
| CARBON | 24.73 | 32.99 | 41.04 |
| SORBITOL | 11.61 | 4.45 | 6.64 |

As shown in the table, the present invention significantly changes the proportions of the HEC, carbon and Sorbitol in the hygroscopic gel, as compared to the prior art. Only the percentages of (TERGITOL) nonyl phenol polyethylene glycol ether and (TRITON) oxyethylated tertiary octylphenol formaldehyde polymer in the prior art mixture fall within the ranges of the present invention.

5. Dipping—Dipping substrate 12 into and lifting it out of hygroscopic gel 16 at a controlled rate, 1 inch/7 seconds, with an extended submersion dwell of 30 seconds, yields a hygristor 10 having a coating of hygroscopic gel that graduates smoothly from a very thin coating at handling portion 24 to a relatively thick coating at its bottom ¼-inch portion 25. Because of the smoothness of the graduation, calibration of hygristor 10 is simplified. A straight needle scratch starting at handling portion 24 is used to adjust the required final resistance of hygristor 10.

Figure 9:
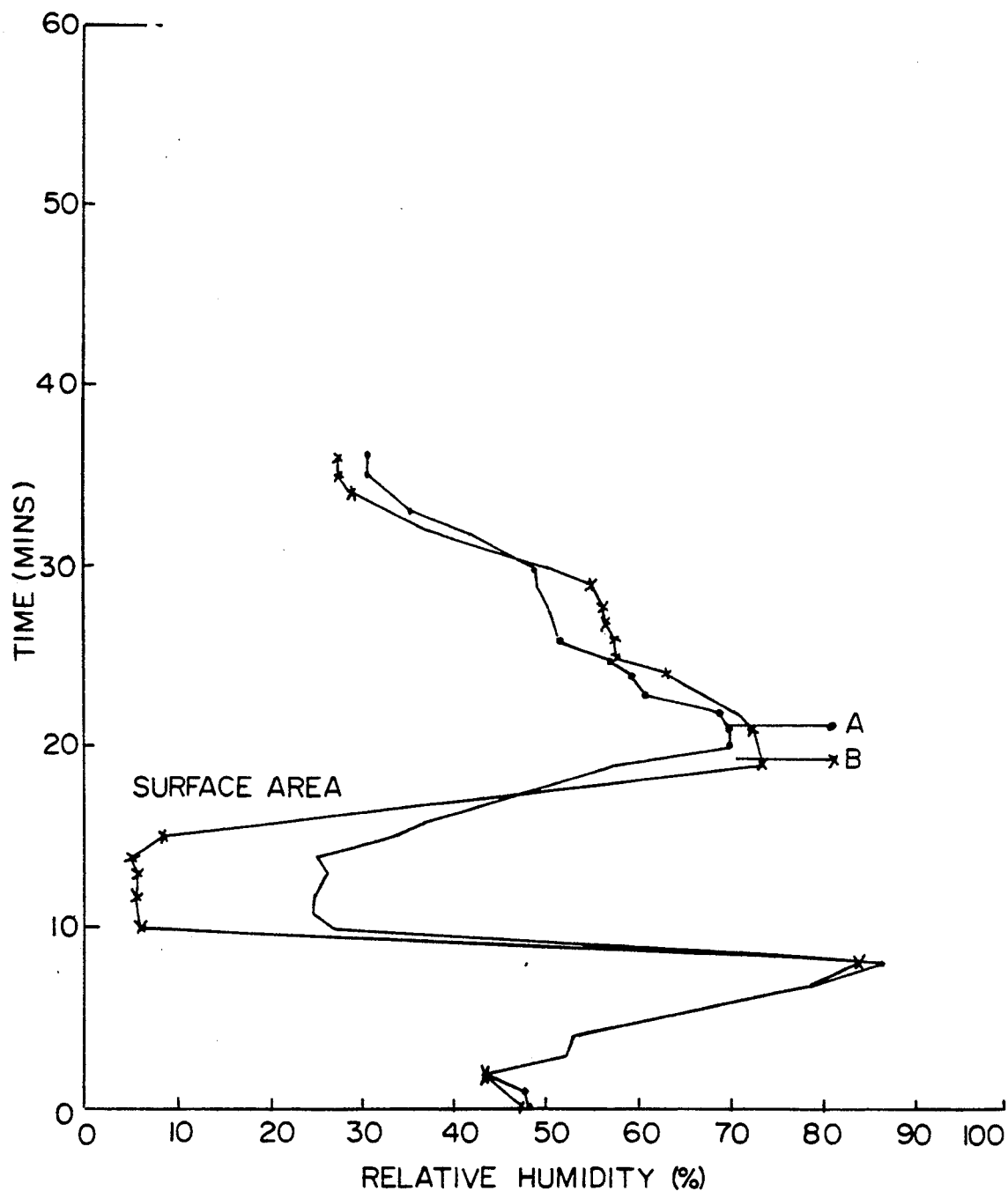
FIG. 9 compares response curves for hygristors manufactured by the method of the present invention and by conventional methods.

Referring to FIG. 9, curve A is a humidity measurement by a prior-art hygristor. Curve B is a humidity measurement by a hygristor of the present invention. The two curves plotted indicate the smoother, faster response of hygristor 10 manufactured using the method of the present invention as compared to a conventionally manufactured hygristor 10. More importantly, the curves indicate that the hygristor manufactured using the method of the present invention displays an extended operating range, that makes it usable between relative humidities of from 5 to 98 percent. The conventionally made hygristor is limited to an operating range of from 20 to 90 percent relative humidity.

Having described the preferred embodiments of the invention with reference to the accompanying drawings, it is to be understood that the invention is not limited to those precise embodiments, and that various changes and modifications may be affected therein by one skilled in the art without departing from the scope or spirit of the invention as defined in the appended claims.

What is claimed is:

1. A method for manufacturing a hygristor comprising:
   preparing a substrate;
   mixing a hygroscopic conductive gel;
   blending said hygroscopic conductive gel for a minimum of 24 hours;
   coating said substrate with said hygroscopic conductive gel; and
   curing said coating.

2. A method for manufacturing hygristors of claim 1, wherein; said step of preparing a substrate includes metallizing opposing edges along a longitudinal axis of said substrate; and forming said substrate of a dielectric material.

3. A method of preparing hygristors of claim 2, wherein the step of metallizing includes metallizing with silver.

4. The method of manufacturing hygristors of claim 1, wherein said mixing of said hygroscopic conductive gel includes mixing together, exclusive of water, the following by percentage of weight:
   hydroxyethylcellulose—from about 19.75 percent to about 25.77 percent;
   nonyl phenyl polyethylene glycol ether, nonyl phenol ethoxylate, anhydrous—from about 2.23 percent to about 3.03 percent;
   oxyethylated tertiary octylphenol formaldehyde polymer—from about 26.94 percent to about 49.92 percent;
   carbon—from about 32.99 percent to about 49.92 percent; and
   Polyethylene Sorbitol—from about 4.45 percent to about 6.64 percent.

5. The method of manufacturing hygristors of claim 1, wherein:
   the step of blending includes ball mining for at least 24 hours.

6. The method of manufacturing hygristors of claim 1, wherein said coating of said substrate includes;
   dipping said hygristor in said hygroscopic conductive gel;
   controlling said dipping at a first controlled rate of at least 7.0 seconds per inch;
   holding said substrate in said hygroscopic conductive gel for a holding time of from about 30 to about 120 seconds; and
   lifting said substrate from said hygroscopic conductive gel at a second controlled rate of from about 8.0 to about 9.0 seconds per inch.

7. The method for manufacturing hygristors of claim 1, further comprising;
   curing said hygristors in a controlled environment; and
   said controlled environment being dust free and being from about 31.0 to about 35.0 relative humidity and from about 23.0 to about 27.0 degrees C.

8. The method for manufacturing hygristors of claim 1, the step of preparing substrates including casting substrates from acrylic resins.

9. The method of manufacturing hygristors of claim 1, the step of preparing substrates including molding substrates from acrylic material.

10. The method of manufacturing hygristors of claim 1, the step of preparing substrates including cutting substrates from a sheet of a plastic resin.

11. The method of manufacturing hygristors of claim 1, further comprising:

adjusting an electrical resistance of said hygristors; and said adjusting including scratching said hygroscopic conductive gel to increase said resistance.

12. The method of manufacturing hygristors of claim 1, further comprising:

adjusting an electrical resistance of said hygristors; and said adjusting includes removing portions of said hygroscopic conductive gel to increase said resistance to a desired value.

13. The method of manufacturing hygristors of claim 1, further comprising:

adjusting an electrical resistance of said hygristors; and said adjusting including abrading said hygroscopic conductive gel.

14. A method of manufacturing hygristors, comprising:

mixing a hygroscopic gel;

said hygroscopic gel including from about from about 32.99 percent to about 41.04 percent carbon, exclusive of a water content of said hygroscopic gel;

milling said hygroscopic gel for a time;

coating a substrate with said hygroscopic gel; and curing said hygroscopic gel.

15. A method according to claim 14, wherein said time is at least 24 hours.

16. A method according to claim 14, wherein the step of mixing includes:

placing all components, including a necessary amount of water, in a container; and ball milling said components for a time effective to produce a smooth mixture.

17. A method according to claim 16, wherein said time is at least 24 hours.

* * * * *